US008242300B2

(12) United States Patent
Gonzalez et al.

(10) Patent No.: US 8,242,300 B2
(45) Date of Patent: Aug. 14, 2012

(54) PROCESS FOR SELECTIVE, PARTIAL, SUBSTANTIALLY SOLVENT-FREE, OXIDATION OF METHANE TO METHANOL AND/OR A METHANOL DERIVATIVE WITH A HETEROGENEOUS CATALYST AND SULFUR TRIOXIDE

(75) Inventors: Michael A. Gonzalez, Sanford, MI (US); Daniel R. Henton, Midland, MI (US); David C. Molzahn, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 240 days.

(21) Appl. No.: 12/670,431

(22) PCT Filed: Jul. 1, 2008

(86) PCT No.: PCT/US2008/068877
§ 371 (c)(1),
(2), (4) Date: Jan. 25, 2010

(87) PCT Pub. No.: WO2009/017925
PCT Pub. Date: Feb. 5, 2009

(65) Prior Publication Data
US 2011/0021802 A1    Jan. 27, 2011

Related U.S. Application Data

(60) Provisional application No. 60/962,310, filed on Jul. 27, 2007.

(51) Int. Cl.
*C07C 27/16* (2006.01)
*C07C 303/06* (2006.01)
*B01J 21/06* (2006.01)
*B01J 27/12* (2006.01)
*B01J 39/04* (2006.01)

(52) U.S. Cl. .......... 558/40; 558/38; 558/39; 558/41; 568/910; 568/910.5; 562/123

(58) Field of Classification Search .......... None
See application file for complete search history.

(56) References Cited

U.S. PATENT DOCUMENTS

| 2,492,983 | A  | 1/1950 | Grosse et al. |
| 2,493,038 | A  | 1/1950 | Snyder et al. |
| 2,553,576 | A  | 5/1951 | Grosse et al. |
| 5,220,080 | A  | 6/1993 | Lyons et al. |
| 5,306,855 | A  | 4/1994 | Periana et al. |
| 2006/0025628 | A1 | 2/2006 | Zerella et al. |
| 2006/0167314 | A1 | 7/2006 | Periana |

FOREIGN PATENT DOCUMENTS

| CN | 1400198 A     | 3/2003 |
| DE | 10132526 A1   | 1/2003 |
| GB | 632820        | 12/1949 |
| WO | WO-2006/091849 A2 | 8/2006 |

OTHER PUBLICATIONS

Frusteri, Francesco et al., "Thin-layer Supported Nafion Catalysts for the Partial Oxidation of Light Alkanes", J. Chem. Soc., Chem. Commun., 1332 to 1334, 1991.*
Mukhopadhyay, Sudipii et al., "A High-Yield, Liquid-Phase Approach for the Partial Oxidation of Methane to Methanol using SO3 as the Oxidant", Adv. Synth.Catal., 2005, 347, 1203-1206.*
Li, Fengbo, et al., Preparation of mesostructured barium sulfate and its application in methane activation, Journal of Catalysis, 2006, pp. 282-289, vol. 239.
Seen, Andrew J., Nafion: an excellent support for metal-complex catalysts, Journal of Molecular Catalysis A:Chemical, 2001, pp. 105-112, vol. 177.
Li, Fengbo, et al., Low temperature catalytic conversion of methane to methanol by barium sulfate nanotubes supporting sulfates: $Pt(SO_4)_2$, $HgSO_4$, $Ce(SO_4)_2$ and $Pb(SO_4)_2$, Chemical Communications, 2005, pp. 2238-2240, vol. 17.
Michalkiewicz, B., et al., The Role of Pressure in the Partial Methane Oxidation Process in the Pd—Oleum Environment, Chemical Papers, 2003, pp. 393-396, vol. 57(6).
Michalkiweicz, Beata, et al., Catalytic system containing metallic palladium in the process of methane partial oxidation, Journal of Catalysis, 2003, pp. 14-19, vol. 215.
Michalkiewicz, B., Methane Conversion to Methanol in Condensed Phase[1], Kinetics and Catalysis, 2003, pp. 801-805, vol. 44, No. 6.
Liyu, Chen, et al., Methane Oxidation over a $V_2O_5$ Catalyst in the Liquid Phase, Energy and Fuels, 2006, pp. 915-918, vol. 20.
De Vos, Dirk, E. et al., Gold Redox Catalysis for Selective Oxidation of Methane to Methanol, Angew. Chem. Int. Ed., 2005, pp. 30-32, vol. 44.
Periana, Roy A., et al., High yield conversion of methane to methyl bisulfate catalyzed by iodine cations, Chemical Communications, 2002, pp. 2376-2377, vol. 20.
Zerella, Mark, et al., Methane oxidation to acetic acid catalyzed by $Pd^{2+}$ cations in the presence of oxygen, Journal of Catalysis, 2006, pp. 111-117, vol. 237.
Periana, Roy A., et al., Homogeneous, catalytic, oxidative coupling of methane to acteic acid in one step, Topics in Catalysis, 2005, pp. 169-174, vol. 32, Nos. 3-4.
Zerella, Mark, et al., Direct oxidation of methane to acetic acid catalyzed by $Pd^{2+}$ and $CU^{2+}$ in the presence of molecular oxygen, Chemical Communications, 2004, pp. 1948-1949, vol. 17.
Periana, Roy A., et al., Catalytic, Oxidative Condensation of $CH_4$ to $CH_3COOH$ in One Step via CH Activation, Science, 2003, pp. 814-818, vol. 301.
Asadullah, Mohammad, et al., Calcium-Catalyzed Selective and Quantitative Transformation of $CH_4$ and CO into Acetic Acid, Angew. Chem. Int. Ed., 2009, pp. 2475-2478, vol. 39, No. 14.
Mukhopadhyay, Sudip, et al., A High-Yield, Liquid-Phase Approach for the Partial Oxidation of Methane to Methanol using $SO_3$ as the Oxidant, Adv. Synth. Catal., 2005, pp. 1203-1206, vol. 347.
Cordoba, Luis Fernando, et al., No reduction by $CH_4$ over Pd/Co-sulfated zirconia catalysts, Applied Catalysis B: Environmental, 2005, pp. 269-277, vol. 56.
Quincoces, C.E., et al., Effect of water vapor over Pd-Co/SZ catalyst for the NO selective reduction by methane, Catalysis Communications, 2005, pp. 75-80, vol. 6.
Kantcheva, Margarita, et al., Cobalt supported on zirconia and sulfated zirconia II. Reactivity of adsorbed $NO_x$ compounds toward methane, Journal of Catalysis, 2004, pp. 364-371, vol. 223.

(Continued)

*Primary Examiner* — Fiona T Powers

(57) ABSTRACT

The present invention relates to selective partial oxidation of methane in the absence of a solvent such as sulfuric acid or oleum.

8 Claims, No Drawings

OTHER PUBLICATIONS

Mukhopadhyay, Sudip, et al., A Novel Method for the Direct Sulfonation of $CH_4$ with $SO_3$ in the Presence of $KO_2$ and a Promoter, Organic Process Research and Development, 2003, pp. 754-757, vol. 7.

Mukhopadhyay, Sudip, et al., Direct catalytic sulfonation of methane with $SO_2$ to methanesulfonic acid (MSA) in the presence of molecular $O_2$, Chemical Communications, 2003, pp. 1590-1591, vol. 13.

Mukhopadhyay, Sudip, et al., Direct Sulfonation of Methane to Methanesulfonic Acid with $SO_2$ Using Ca Salts as Promoters, J. Am. Chem. Soc., 2003, pp. 4406-4407, vol. 125.

Mukhopadhyay, Sudip, et al., Direct Sulfonation of Methane to Methanesulfonic Acid by Sulfur Trioxide Catalyze by Cerium(IV) Sulfate in teh Presence of Molecular Oxygen, Adv. Synth. Catal., 2004, pp. 913-916, vol. 346.

Basickes, Naomi, et al., Radical-Initiated Functionalization of Methane and Ethane in Fuming Sulfuric Acid, J. Am. Chem. Soc., 1996, pp. 13111-13112, vol. 118.

Mukhopadhyay, Sudip, et al., Effects of Solvent Acidity on the Free-Radical-Initiated Synthesis of Methanesulfonic Acid from $CH_4$ and $SO_3$, in Eng. Chem. Res., 2002, pp. 5901-5905, vol. 41.

Mukhopadhyay, Sudip, et al., A High-Yield Approach to the Sulfonation of Methane to Methanesulfonic Acid Initiated by $H_2O_2$ and a Metal Chloride, Angew. Chem. Int. Ed., 2003, pp. 2990-2993, vol. 42.

Seen, Andrew J., Nafion: an excellent support for metal-complex catalysts, Journal of Molecular Catalysis A: Chemical, 2001, pp. 105-112, vol. 177.

Conley, Brian L., et al., Design and study of homogeneous catalysts for the selective low temperature oxidation of hydrocarbons, Journal of Molecular Catalysis A: Chemical, 2006, pp. 8-23, vol. 251.

Olah, George A., et al., Selective Monohalogenation of Methane over Supported Acid or Platinum Metal Catalysts and Hydrolysis of Methyl Halides over γ-Alumina-Supported Metal Oxide/Hydroxide Catalysts. A Feasible Path for the Oxidative Conversion of Methane into Methyl Alsohol/Simethyl Ether[1], J. Am. Chem. Soc., 1985, pp. 7097-7105. vol. 107.

Martins, Ruth L., et al., Methane activation on superacidic catalysts based on oxoanion modified zirconium oxide, Applied Catalysis A: General, 2006, pp. 143-152, vol. 308.

Michalkiewicz, B., The kinetics of homogeneous catalytic methane oxidation, Applied Catalysis A: General, 2006, pp. 270-274, vol. 307.

Arata, Kazushi, et al., Synthesis of solid superacids and their activities for reactions of alkanes, Catalysis Today, 2003, pp. 17-30, vol. 81.

Lowry, Thomas H. et al., Influence of Solvent, Nucleophile, Leaving Group, and Substrate Structure, Mechanism and Theory in Organic Chemistry, 1981, p. 363, Second Edition, Harper & Row, Publishers, New York.

International Search Report (PCT/US2008/068877).

* cited by examiner

PROCESS FOR SELECTIVE, PARTIAL, SUBSTANTIALLY SOLVENT-FREE, OXIDATION OF METHANE TO METHANOL AND/OR A METHANOL DERIVATIVE WITH A HETEROGENEOUS CATALYST AND SULFUR TRIOXIDE

This application claims the benefit of U.S. Provisional Application No. 60/962,310 filed Jul. 27, 2007.

The present invention relates generally to a process for production of methanol and methanol derivatives such as its sulfate ester(s), with emphasis upon partial oxidation of methane to methanol derivatives by gas-phase oxidation of methane. Production of methanol typically includes a hydrolysis step, for example a reactive contact between a sulfate salt and water. As used herein, "gas-phase oxidation" refers to oxidation that occurs substantially without, preferably completely without, use of a conventional methane oxidation solvent such as sulfuric acid ($H_2SO_4$). The present invention relates more particularly to such a process wherein oxidation is both selective and partial, thereby limiting production of full oxidation products such as carbon dioxide ($CO_2$). The present invention relates still more particularly to use of a heterogeneous catalyst comprising a transition metal, preferably palladium, and an acid catalyst, preferably a perfluorosulfonic acid catalyst (for example NAFION® SAC-13 (a perfluorinated sulfonic acid polymer on a silica support commercially available from E. I du Pont de Nemours and Company for use as, for example an ion exchange membrane), and optionally, but preferably, a support (for example silica or alumina) for perfluorosulfonic acid catalysts that do not already contain such a support. The present invention also relates to use of sulfur trioxide ($SO_3$) as an oxidizing agent. The methanol and sulfate ester(s) produced in the said process may be used in any conventional application for methanol ($CH_3OH$), to include preparation of methanol derivatives.

The ability to directly convert methane to methanol and/or a methanol derivative in economically satisfactory yields is an important goal of the oil and gas industry. Methane is an abundant material found world-wide, particularly in the form of natural gas. As a gas, it is difficult and costly to transport. Conversion to the liquid methanol allows for safer, more efficient transportation. In addition, methanol is a valuable commercial feedstock, an important ingredient in the production of reformulated motor fuels, and an environmentally compatible fuel in itself.

Conversion of raw hydrocarbons into commercially more useful materials currently uses multi-step and/or high temperature, typically above 300 degrees centigrade (° C.), processes. This leads to expensive reactors, extensive heat management challenges and subsequent high capital and operating costs. In conversions developed to date, a key chemical challenge is the direct, selective conversion of C—H or CC bonds of hydrocarbons at temperatures lower, preferably much lower, than 300° C. to produce functional bonds such as C—OH, C=C, other C—C or other C—X bonds where X is a hetero atom (for example sulfur (S), nitrogen (N) or phosphorous (P)), or halogen (for example fluorine (F), chlorine (Cl) or bromine (Br)). In general, present oxidation catalyst technology for C—H and C—C conversion is not sufficiently selective to allow direct conversion processes due to the involvement of radical and especially free radical reaction pathways.

A conventional method for catalytic conversion of methane ($CH_4$) to methanol ($CH_3OH$) involves an initial reaction of $CH_4$ with water to produce synthesis gas (a mixture of carbon monoxide and hydrogen), followed by catalytic conversion of the synthesis gas to methanol. A direct, one-step oxidation of methane to methanol would be simpler, and economically and environmentally preferable.

Certain catalysts that contain oxidation-active transition metals (for example platinum palladium or vanadium) tend to produce carbon monoxide (CO) and carbon dioxide ($CO_2$) as further oxidation products, rather than significant amounts of methanol, when used in conjunction with molecular oxygen ($O_2$) as an oxidant. This may stem, at least in part, from an observation that further oxidation of methanol with molecular oxygen appears to be both kinetically and thermodynamically favored over methanol production at elevated oxidation temperatures such as above 250° C.

U.S. Pat. No. 5,220,080 (Lyons et al.) discloses a process for direct catalytic oxidation of methane ($CH_4$) to methanol ($CH_3OH$) that comprises contacting a light alkane (for example $CH_4$) with an oxidant (for example air) in the presence of a catalyst comprising a surface oxide chromate in which chromium is chemically bound to oxygen of a metal oxide support surface.

U.S. Pat. No. 5,306,855 (Periana et al.) teaches a catalytic oxidation process for converting lower alkanes into alkyl oxy-esters which may be converted into hydrocarbons (desirably in the gasoline boiling range) or alcohols. The process involves contacting a lower alkane (for example methane) with an acid, a catalyst and an oxidizing agent (for example oxygen and/or sulfuric acid ($H_2SO_4$)).

U.S. Pat. No. 2,492,983 (Grosse et al.) discloses preparation of methanol by decomposing methane sulfonic acid ($CH_4O_3S$), either by pyrolysis or thermal decomposition at temperatures such as 225° C. up to 500° C. Grosse et al. refers to U.S. Pat. No. 2,493,038 for preparation of methane sulfonic acid via direct sulfonation of methane with sulfur trioxide ($SO_3$).

U.S. Pat. No. 2,493,038 (Snyder et al.) teaches use of a sulfonation catalyst that comprises a metal or a sulfate of a metal in Group II-B of the Periodic Table, especially mercury (Hg), to catalyze a reaction between methane and $SO_3$ at a temperature within a range of from 100° C. to 450° C. Snyder et al. notes that reaction condition selections, including a pressure of from atmospheric to 5000 psig (34,474 kPa) are less severe than those under which methane is completely oxidized to inorganic carbon oxides, specifically carbon monoxide (CO) and carbon dioxide ($CO_2$). Snyder et al. employs a molar excess of methane over $SO_3$ when favoring formation of oxygenated products such as methanol in the form of its esters.

G. A. Olah et al., in "Selective Monohalogenation of Methane over Supported Acid or Platinum Metal Catalysts and Hydrolysis of Methyl Halides over γ-Alumina-Supported Metal Oxide/Hydroxide Catalysts. A Feasible Path for the Oxidative Conversion of Methane to Methyl Alcohol/Dimethyl Ether", *Journal of the American Chemical Society*, volume 107, pages 7097-7105 (1985), teach catalytic monohalogenation (chlorination or bromination) of methane over either a supported solid acid catalyst, such as NAFION®-H/tantalum fluoride, or a supported platinum metal catalyst, such as Pd on barium sulfate, at a temperature between 180° C. and 250° C. Subsequent hydrolysis of monohalogenated methane yields methanol (methyl alcohol or $CH_3OH$).

Martins et al., in "Methane activation on superacidic catalysts based on oxoanion modified zirconium oxide", *Applied Catalysis A: General*, volume 308, pages 143-152 (2006), characterizes a "superacid" as any acid that has an acidity stronger than that of 100% $H_2SO_4$.

A. J. Seen, in "Nafion: an excellent support for metal-complex catalysts", *Journal of Molecular Catalysis A:*

*Chemical*, volume 177, pages 105-112 (2001), notes that supported catalyst activity depends on metal-complex loading in NAFION. Seen focuses efforts upon use of NAFION as a support for cationic Pd (II) catalysts for dimerization of ethene (ethylene).

Michalkiewicz et al., in "Catalytic system containing metallic palladium in the process of methane partial oxidation", *Journal of Catalysis*, volume 215, pages 14-19 (2003), teaches oxidation of methane to organic oxygenates over metallic palladium dissolved in oleum (30% sulfur trioxide in fuming sulfuric acid). Methanol production begins with transformation of methane into methyl bisulfite and dimethyl sulfate and concludes with ester hydrolysis.

Michalkiewicz, in "The kinetics of homogeneous catalytic methane oxidation", *Applied Catalysis A: General*, volume 307, pages 270-274 (2006), presents a platinum-catalyzed system using oleum as a reaction medium for oxidizing methane to methyl bisulfate ($CH_3OSO_3H$).

Mukhopadhyay et al., in "A High-Yield, Liquid-Phase Approach for the Partial Oxidation of Methane to Methanol using $SO_3$ as the Oxidant", *Adv. Synth. Catal.*, volume 347, pages 1203-1206 (2005), discloses a three step, direct approach for producing $CH_3OH$ from $CH_4$. Their approach begins by reacting methane with $SO_3$ to form methane sulfonic acid (MSA) at 75° C. using a free-radical initiator (for example a urea-peroxide combination with rhodium chloride) and MSA as the solvent.

As used throughout this specification, definitions presented in this paragraph, in succeeding paragraphs or elsewhere in the specification, have meanings ascribed to them where first defined. Accordingly, "catalyst", as used herein, refers to a chemical agent that facilitates a chemical method or process. In one embodiment of the invention, the term is used to describe a reagent used to activate a hydrocarbon C—H bond. In another embodiment, the term refers to a substance that initiates or accelerates a chemical reaction without itself being affected. Catalysts facilitate the chemical reactions between hydrocarbons, oxidants, solvents and other components of a chemical transformation.

The term "hydrocarbon C—H bond" as used herein refers to a covalent bond between hydrogen and carbon localized within a hydrocarbon molecule. A C—H bond may be described in terms of frontier molecular orbital theory as having a highest occupied molecular orbital (HOMO) and a lowest unoccupied molecular orbital (LUMO).

The term "oxidant" refers to a compound that oxidizes (removes electrons from) another substance in a chemical oxidation, reaction, process or method. In doing so, the oxidizing agent, sometimes called an oxidizer or oxidant, becomes reduced (gains electrons) in the process. An oxidizing chemical reaction is broadly defined and may have several meanings. In one definition, an oxidizing agent receives (accepts) electrons from another substance (reductant). In this context, the oxidizing agent is called an electron acceptor. Broadly speaking, such chemical events occur in two distinct ways which can be described as inner sphere or outer sphere. In another meaning, an oxidant transfers O (oxygen) atoms to the reductant. In this context, the oxidizing agent can be called an oxygenation reagent or oxygen-atom transfer agent. Sulfur trioxide ($SO_3$) constitutes a preferred oxidant for purposes of the present invention.

The term "strongly acidic", when used herein with respect to a catalyst material, means sufficiently strong to facilitate activation of C—H bonds contained in hydrocarbons such as methane towards reaction with $SO_3$ (for example via carbocations). Acidic catalyst materials, especially strongly acidic catalyst materials, may be an acid classified as a Lewis acid (for example antimony fluoride ($SbF_5$)) or an acid classified as a Lowry-Brönsted acid. See also Lowry and Richardson, Mechanism & Theory in Organic Chemistry", page 363, (Harper & Row publishers, Inc.), (1981).

A primary aspect of the present invention is a process for selective, partial oxidization of methane, the process being a substantially solvent-free process that comprises placing sulfur trioxide and gaseous methane in operative contact with an acidic catalyst material, preferably a solid acidic catalyst material and more preferably a solid, strongly acidic catalyst material, the contact occurring at a combination of temperature, methane pressure and for a length of time sufficient to convert at least a portion of non-gaseous forms of such sulfur trioxide to gaseous sulfur trioxide and selectively and partially oxidize at least a portion of the methane to at least one partial oxidation product selected from a group consisting of methanol and methanol derivatives.

The portion of selectively and partially oxidized methane represents a partial oxidation product yield that is preferably more than one mole percent (mol %), more preferably at least (greater than or equal ($\geq$)) to 1.5 mol % and even more preferably $\geq$three mol %, in each case based upon moles of sulfur trioxide. As product yield increases, process economics improve. Accordingly, product yields of $\geq$5 mol %, $\geq$7 mol %, $\geq$10 mol % and $\geq$12 mol % being increasingly more desirable. The product yield may be as much as 100 mol % in an ideal reaction, but is more likely less than or equal to 95 mol %, with increasing likelihood of yields that are less than or equal to 90 mol %, less than or equal to 85 mol %, less than or equal to 80 mol %, less than or equal to 75 mol %, and less than or equal to 70 mol %, in each case based upon moles of sulfur trioxide.

The process may be run as a batch process, a continuous process or a semi-batch process. The latter is a hybrid of the batch and continuous processes that incorporates some features of each.

"Operative contact", as used herein, means placing sulfur trioxide, at least a portion of which is in gaseous form, and gaseous methane, in contact with at least a reactive surface portion of a solid, acidic catalyst material, preferably a solid, strongly acidic catalyst material, under conditions of temperature and methane pressure sufficient to partially and selectively oxidize at least a portion of the methane to a methanol derivative.

The catalyst material is a solid catalyst material, preferably, a solid acidic catalyst material, more preferably, a solid, strongly acidic catalyst material that comprises a perfluorinated organo-sulfonic acid moiety, and is more preferably a material that comprises a perfluorinated organic polymer, and still more preferably a perfluorinated organo-sulfonic acid polymer (for example NAFION® SAC 13, marketed by E. I. du Pont de Nemours and Company as an ion exchange polymer). The catalyst material also preferably comprises a transition metal, with a combination of a polymer having an organo-sulfonic acid moiety, perfluorinated and sulfonated organic polymer or perfluorinated organo-sulfonic acid polymer, whichever is appropriate, and a transition metal sometimes being referred to as a "heterogeneous catalyst" or a "heterogeneous superacid catalyst". The transition metal is preferably deposited upon at least a surface portion of, for example, the perfluorinated organo-sulfonic acid polymer, preferably a perfluorinated and sulfonated organic polymer. The transition metal preferably has a capacity to activate methane carbon-hydrogen (C—H) bonds and is more preferably selected from a group consisting of palladium (Pd), vanadium (V), cerium (Ce), platinum (Pt), copper (Cu), iridium (Ir), tantalum (Ta), and niobium (Nb), but is preferably Pd. Other transition metals that have a capacity to activate methane C—H bonds may be used if desired, possibly with less effectiveness than the aforementioned group. The catalyst material preferably further comprises a metal oxide support surface wherein the metal is selected from silicon, aluminum, magnesium, titanium, zirconium and mixtures thereof. See U.S. Pat. No. 5,220,080 (Lyons et al.) discussed above and incorporated herein by reference, for teachings about such metal oxide support surfaces.

Solid, strongly acidic catalyst materials that contain an organo-sulfonic acid moiety include perfluorinated organo-sulfonic acid polymers (for example those marketed under trade name NAFION™, especially NAFION™ SAC-13 noted above) as well as sulfated zirconias, aluminosilicates (for example ZMS-5, commercially available from Zeolyst International), gamma alumina, silicoaluminophosphates (for example SAPO-34, commercially available from UOP), and mordenite zeolites.

By way of illustration using a heterogeneous catalyst comprising a perfluorinated organo-sulfonic acid polymer to provide the organo-sulfonic acid moiety and Pd as the transition metal, a preferred Pd loading ranges from greater than one percent by weight (wt %) to less than or equal to four wt %, each wt % being based upon total supported catalyst weight. The Pd loading more preferably ranges from greater than or equal to 2.2 wt % to less than or equal to 3 wt %, and still more preferably from greater than or equal to 2.4 wt % to less than or equal to 2.9 wt %, each wt % being based upon total supported catalyst weight. Skilled artisans can readily determine preferred loadings of Pd on other catalyst supports as well as preferred loadings of other metals noted above with either a perfluorinated organo-sulfonic acid polymer or another catalyst that contains a perfluorinated organo-sulfonic acid moiety without undue experimentation using the guidance provided relative to Pd on a perfluorinated organo-sulfonic acid polymer.

The contact of gaseous methane ($CH_4$) and sulfur trioxide ($SO_3$) with the acidic catalyst material, especially a strongly acidic catalyst material, preferably occurs at a temperature sufficient to facilitate catalytic activation of methane C—H bonds toward a reaction with $SO_3$, (typically at least 100° C., preferably at least 125° C., more preferably at least 150° C. and still more preferably at least 175° C., yet less than a temperature at which the acidic catalyst material becomes unstable (typically no more than about 230° C. as higher temperatures, while effective with at least some acidic catalyst materials, are not needed to effect selective partial oxidation of methane). Satisfactory results also occur, particularly with a superacid catalyst selected from a perfluorinated organo-sulfonic acid polymer, a composite of a perfluorinated organo-sulfonic acid polymer and a porous inorganic support, and a supported catalyst, the supported catalyst comprising a transition metal selected from a group consisting of palladium, vanadium and cerium on a composite of a perfluorinated organo-sulfonic acid polymer and a porous inorganic support, at a temperature of no more than 220° C., preferably no more than 215° C., still more preferably no more than 210° C. and even more preferably no more than 200° C. This temperature is also typically sufficient to convert at least a portion of non-gaseous (that is solid, liquid or a mixture thereof) $SO_3$ to gaseous $SO_3$. An additional reason to avoid temperatures higher than that at which the acidic catalyst material becomes unstable is that such higher temperatures tend to promote formation of complete or nearly complete oxidation products (for example CO and $CO_2$ as taught by Snyder et al. in U.S. Pat. No. 2,493,038 (discussed above).

The contact preferably occurs at a methane ($CH_4$) pressure, measured at a temperature within a temperature range of from 150° C.), within a range of from (25 pounds per square inch gauge (psig) (170 kilopascals (KPa)) to 2000 psig (13,790 6,895 KPa) for a length of time (sometimes referred to as "residence time") that is less than a time sufficient to completely convert methane to at least one of carbon monoxide and carbon dioxide, its full oxidation products. The residence time is preferably within a range of from greater than 30 seconds five minutes to less than or equal to 100 hours. The methane pressure, measured at a temperature of 150° C., more preferably lies within a range of from 150 psig (1034 KPa) to 1500 psig (10,342 KPa), still more preferably within a range of from 250 psig (1724 KPa) to 1000 psig (6,895 KPa), and even more preferably from 500 psig (3447 KPa) to 1000 psig (6,895 KPa). The period of time or residence time more preferably lies within a range of from 5 minutes to 6400 minutes, still more preferably within a range of from 30 minutes to 300 minutes and even more preferably within a range of from 30 minutes to 90 minutes.

Skilled artisans recognize that on the laboratory scale handling non-gaseous forms of $SO_3$ (liquid and solid) has practical advantages over handling gaseous sulfur trioxide, with solid sulfur trioxide being easier than both liquid and gaseous forms of sulfur trioxide. Skilled artisans also recognize that two or more forms of $SO_3$ can, and often do, co-exist (for example solid, liquid and gas forms of $SO_3$). Skilled artisans also recognize that one may influence which forms of an amount of $SO_3$ are present in a closed vessel by choosing a temperature and a pressure and exposing the $SO_3$ to that temperature and pressure.

The process of the present invention employs a substantially, more preferably a completely, solvent-free (within analytical determination limits and in the absence of adding a solvent, especially a strong liquid acid, to a reaction zone) as well as a predominantly if not substantially or more preferably a completely gas phase oxidation reaction as opposed to liquid phase oxidation which mandates use of a strong liquid acid such as concentrated sulfuric acid ($H_2SO_4$), fuming $H_2SO_4$ or oleum. While some $SO_3$ may be present in a condensed (for example liquid) phase, condensed $SO_3$ does not constitute a solvent for purposes of this invention.

Gas phase oxidations within the scope of this invention are preferably mono-oxidation reactions that beneficially and, more often, preferably use a super acid catalyst (SAC). While a number of superacid catalysts exist, such as oxoanion modified zirconias (for example sulfated, molybdated, tungstated zirconias as disclosed in *Applied Catalysis A General* 308 (2006) 143-152 and *Catalysis Today* 81 (2003) 17-30), per-fluorinated ion exchange polymers, and those enumerated by Olah in his article entitled, "Selective Monohalogenation of Methane over Supported Acid or Platinum Metal Catalysts and Hydrolysis of Methyl Halides over γ-Alumina-Supported Metal Oxide/Hydroxide Catalysts. A Feasible Path for the Oxidative Conversion of Methane into Methyl Alcohol/Dimethyl Ether", *Journal of the American Chemical Society* (JACS), volume 107, pages 7097-7105 (1985), preferred results occur with use of a perfluorinated organo-sulfonic acid polymer (NAFION® SAC, E. I. du Pont de Nemours and Company) as a component of a catalyst support for a transition metal. NAFION® SAC-13, a strongly acidic, supported catalyst material comprising a loading of 10% to 20% NAFION® polymer on a silica support (sometimes referred to as a "porous nanocomposite"), provides especially preferred results.

The oxidizing agent is $SO_3$, preferably $SO_3$ in a substantially non-gaseous form (for example solid and/or liquid) for ease of handling, functions as a preferred oxidizing agent, especially when used in conjunction with the SAC/transition metal combinations noted herein and in accord with operating parameters and conditions disclosed herein. The $SO_3$ is preferably present in an amount that provides a high selectivity to partial oxidation products, such as a methanol derivative, while minimizing formation of over-oxidation products, specifically CO and $CO_2$. The amount is preferably within a range of from one tenth (0.1) of a mole of $CH_4$ per 1 mole of $SO_3$ to 10 moles of $CH_4$ per 1 mole of $SO_3$ ($CH_4:SO_3$ molar ratio of 0.1:1 to 10:1), more preferably within a range of from one mole of $CH_4$ to five moles of $SO_3$ ($CH_4:SO_3$ molar ratio of 1:1 to 5:1), and still more preferably from two moles of $CH_4$ per mole of $SO_3$ to five (5) moles of $CH_4$ per mole of $SO_3$ ($CH_4:SO_3$ molar ratio of 2:1 to 5:1).

Analytical Procedures

The analytical procedure used for $^1H$ NMR is based on a standard method such as described in an ACS Professional Reference Book entitled "Spectroscopy of Polymers" by Jack L. Koening. Prepare sample aliquots from the examples presented below for $^1H$ NMR analysis by first removing solids, to the extent necessary to do so, via filtration using a Whatman 0.45 micrometer (μm) PURADISC™ 25Nyl filter. Combine an amount, typically 1 to 1.5 g, of the sample aliquot with 100 milligrams (mg) of glacial acetic acid as an internal standard and 0.2 milliliters (mL) of deuterium oxide ($D_2O$) as a lock solvent. Use a Bruker Biospin™ AVANCE™ 300 MHz Nuclear Magnetic Resonance Spectrometer (serial number BH045999), with a 5 mm QNP $^1H/^{13}C/31P/^{19}F$ Probe (Serial number Z8352/0008) for the $^1H$ NMR analysis.

Perform duplicate sample preparation and analysis and average $^1H$ NMR analytical results. Make structural assignments for $^1H$ NMR peaks based upon chemical shifts relative to acetic acid, assigning 2.04 parts per million (ppm) to acetic acid, 3.3 ppm to methanol ($CH_3OH$), 3.7 ppm to methylsulfuric acid (methyl hydrogen sulfate or $CH_3OSO_3H$), 2.8 ppm to methanesulfonic acid (methylsulfonic acid or $CH_3SO_3H$) and 4.3 ppm to methyl bisulfite ($CH_2(SO_3H)_2$).

Calculate amount of $CH_3OX$ (where X=hydrogen or a sulfonic acid moiety) as follows:

Mmol of $CH_3OX$=1.000 mmol/mol multiplied by ($CH_3OX$ peak area divided by acetic acid peak area) multiplied by (weight (in grams (g)) of added acetic acid added divided by molecular weight of acetic acid (60 grams per mole)) multiplied by (total quench sample weight divided by amount of added quench sample (for example 1 g to 1.5 g)).

"$CH_3OX$ peak area" represents combined areas for methanol and methylbisulfite.

"Quench sample weight" is total weight of liquid obtained from the Parr reactor (for example Ex 1 below).

The following examples illustrate, but do not limit, the present invention. All parts and percentages are based upon weight, unless otherwise stated. All temperatures are in ° C. Examples (Ex) of the present invention are designated by Arabic numerals and Comparative Examples (Comp Ex) are designated by capital alphabetic letters. Unless otherwise stated herein, "room temperature" and "ambient temperature" are nominally 20° C.

Catalyst Preparation

Aldrich supplies the following materials used in catalyst preparation: NAFION™ SAC-13 rods; palladium acetate; vanadyl sulfate tri- to penta-hydrate ($VO(SO_4).3$-$5H_2O$); zirconium sulfate monohydrate ($Zr(SO_4).H_2O$); zirconium (IV) hydroxide (sulfated) ($H_4O_{16}S_4Zr$); and cerium sulfate ($Ce(SO_4)_2$).

Procedure A

Place a 10.1 g aliquot of perfluorosulfonic acid catalyst (NAFION™ SAC-13, Aldrich) (~1.5 mmols $SO_3H$, based on 0.15 milli-equivalents/g, 6 mL of pore volume based on 0.6 mL/g) under high vacuum (<10 mm Hg) at ambient temperature for approximately one-half hour (0.5 hr) to yield a dried aliquot. Separately filter a mixture (dark turbid color) consisting of 0.515 g (2.3 mmol) of palladium (II) acetate and 10.5 ml of methylene dichloromethane ($CH_2Cl_2$) through a 0.45 micrometer (um) GHP ACRODISK™ GF (Gelman) filter to produce a dark colored, visually homogeneous $CH_2Cl_2$ solution. Use the $CH_2Cl_2$ solution to wet the dried aliquot, thereby yielding a "wetted catalyst", using up to five (5) ml of $CH_2Cl_2$ to aid in the transfer and distribution of the $CH_2Cl_2$ solution. Place the wetted catalyst under high vacuum (<10 mm Hg) at ambient temperature overnight (approximately 12 hrs) to yield 10.3 g of a tan/light brown solid that has an estimated nominal palladium (Pd) content of ~2.4 wt %, based upon total solid weight.

Procedure B

Replicate Procedure A with changes to provide a higher nominal Pd content. Increase the quantity of perfluorosulfonic acid catalyst to 20.6 g (3.09 mmols) and increase the time under vacuum to approximately one and one half hours (1.5 hr), with occasional heating using a 1200 watt hot air gun (MHT Products Inc., Model Number 500) to speed dried aliquot production. Increase mixture amounts to 1.26 g (5.6 mmol) of palladium (II) acetate and approximately 20 ml of methylene chloride (28.0 g total) to yield 27.1 g of dark colored, visually homogeneous, methylene chloride solution. Use all of the solution to wet the dried aliquot. Decant excess liquid to give 39.3 g of wetted catalyst. Expose the wetted catalyst to a gaseous nitrogen flush for a period of ten minutes to evaporate at least a portion of excess solvent from the wetted catalyst. Dry the wetted catalyst to constant weight under high vacuum (<10 mm Hg) with occasional heating using the hot air gun over a period of approximately 1.5 hr, to yield 20.4 g of tan/light brown solid with an estimated nominal Pd content of 2.9 wt %, based upon total solid weight.

Procedure C

Wet a 6.93 g aliquot of tan/light brown solid produced in accord with Procedure B with 4.32 g of 1 N sulfuric acid (1 Normal $H_2SO_4$). Place the wetted solid under vacuum as in Procedure A, but increase the time at ambient temperature to approximately 65 hours (hr), thereby yielding 6.98 g of solid catalyst material.

Procedure D

In a flask situated in a bath heated to a set point temperature of 80° C. and equipped with vacuum take off and septa, place a 10.0 g aliquot of perfluorosulfonic acid catalyst and subject it to vacuum treatment as in Procedure A. The vacuum treatment results in a weight loss of 0.5 g (determined after breaking the vacuum with nitrogen) and yields a white solid material. Treat the white solid material with 6.91 g of aqueous vanadyl sulfate $VO(SO_4)$ (an aqua blue solution prepared from 1.01 g vanadyl sulfate tri to penta hydrate ($VO(SO_4).3$-$5\times H2O$) and 9.75 g of deionized water) to yield a wetted solid. Dry the wetted solid under vacuum as in Procedure A, but do so at a set point temperature of 80° C. for 2.5 hr to yield 10.2 g of blue solid.

Procedure E

Prepare a suspension using 1.56 g of 1N $H_2SO_4$, 0.5 g of cerium sulfate ($Ce(SO_4)_2$) and 4.44 g of deionized water (total suspension weigh equals 6.50 g) that has a turbid yellow color even with sonication for 30 minutes and addition of five drops of 1N $H_2SO_4$. Filter the suspension through a 0.22 um nylon filter to remove solid material and yield 6.5 g of yellow solution. Use the solution to convert 10.55 g of perfluorosulfonic acid catalyst to a wetted solid. Subject the wetted solid to vacuum treatment as in Procedure A at ambient temperature for approximately 12 hours, then at a set point temperature of 50° C. for 1 hr and finally at a set point temperature of 100° C. for approximately two and one half hours (2.5 hr) or until the solid (yellow) maintains a constant weight of 10.55 g.

Procedure F

Use a colorless solution of 0.49 g of zirconium sulfate monohydrate $(Zr(SO_4)_2.H_2O$ in 7.12 g of deionized water to wet 10.07 g of perfluorosulfonic acid catalyst, thereby yielding a wetted material. Dry the wetted material for approximately four hours (4 hr) at a set point temperature of 100° C. to yield a white solid material that has a constant weight of 10.13 g.

Procedure G

Pass a mixture (dark, turbid) of 0.948 g of $Pd(OAc)_2$ (palladium acetate) and 20.7 g of methylene chloride through a filter as in Procedure A, but with a filter pore opening of 0.25 um, to yield 20.5 g of homogeneous dark solution. Prepare a slurry of the solution and 19.8 g of sulfated zirconium (IV) hydroxide. Concentrate the slurry using a rotary evaporator under water aspirator vacuum. Should clumping occur during concentration, re-slurry solids with 20 ml of methylene chloride and repeat concentration with the rotary evaporator. In either event, rotary evaporation results in 20.0 g of a darkened powder. Calcine the powder by heating it in an air oven to a set point temperature of 600° C. over a period of two hours (2 hrs), maintaining the oven and its contents at the set point temperature for three hours (3 hrs) before allowing to cool overnight (approximately 12 hours) to yield 13.5 g of brownish solid. Attribute difference in weight between the darkened powder and the brownish solid to transfer losses and losses during rotary evaporation.

Procedure H

Use a commercially available 4×10 mesh (nominal screen opening of 2 mm by 4.76 mm) carbon supported Pd catalyst with a Pd metal loading of 1 wt % (Mallinckrodt).

Procedure I

Use a commercially available alpha-alumina supported Pd catalyst having a Pd metal loading of 0.5 wt % (Engelhard Industries).

Procedure J

Dissolve 4.5 g of hydrated cerium sulfate $(Ce(SO_4)_2.H_2O)$ in 15.5 g of deionized water to prepare a cerium solution. Use 5.1 g of the cerium solution to impregnate 13.2 g of uncalcined zirconium hydroxide oxide $(ZrO(OH)_2)$ thereby yielding an impregnated material. Calcine the impregnated material by heating it from a set point temperature of 25° C. to 125° C. over a period of one hour, maintain it at a set point temperature of 125° C. for two hours, then heat it to a set point temperature of 600° C. over a period of four hours, hold it at that set point temperature for four hours, then cool it to a set point temperature of 130° C. over a period of three hours, then hold it at that temperature until removing it from the oven and transferring it to a dessicator for further cooling to ambient temperature. The calcined material has a weight of 11.4 g.

Procedure K

Replicate Procedure A with changes to provide a lower nominal Pd content. Increase perfluorosulfonic acid catalyst aliquot size to 10.5 g (~1.6 mmols), but use it as received (without drying or use of applied vacuum. The palladium (II) acetate/methylene chloride mixture contains 10 mg (0.045 mmol) of palladium (II) acetate and approximately 8 ml of methylene chloride. After filtering, the mixture yields a visually homogeneous, light yellow solution that has a weight of 11 g. Use all of the solution to wet the dried aliquot. Dry the wetted catalyst to constant weight at a set point temperature of 80° C. to yield 20.08 g of off-white solid with an estimated nominal Pd content of 0.05 wt %, based upon total solid weight.

Procedure L

Replicate Procedure K with changes to provide a lower nominal Pd content. Decrease perfluorosulfonic acid catalyst aliquot size to 10.0 g (~1.5 mmols). The palladium (II) acetate/methylene chloride mixture contains 107.6 mg (0.479 mmol) of palladium (II) acetate and approximately 7.5 ml of methylene chloride. After filtering, the mixture yields 10 g of visually homogeneous methylene chloride solution. Drying as in Procedure K yields 9.4 g of light yellow solid with an estimated nominal Pd content of 0.54 wt %, based upon total solid weight.

Procedure M

Dissolve 643 mg (2.29 mmol) of hydrated cobalt sulfate $(CoSO_4.7H_2O)$ (commercially available from Mallinckrodt) in 10.0 g of deionized water with sonication at a set point temperature of 50° C. to give a red solution. After cooling the solution to ambient temperature, pipette the solution onto a perfluorosulfonic acid aliquot catalyst that weighs 10.0 g (1.5 mmol), making an effort to wet all of the catalyst. Drying as in Procedure K yields 10.1 g of purple solid with an estimated nominal Co content of 1.35 wt %, based on total solid weight.

Procedure N

Replicate Procedure M with changes to prepare a manganese (Mn) containing catalyst. First, substitute 383 mg (2.27 mmol) of hydrated manganese sulfate $(MnSO_4.7H_2O)$ (commercially available from Aldrich) for the hydrated cobalt sulfate. Second, eliminate sonication, use of a 50° C. set point temperature and cooling to ambient temperature. Preparation of wetted catalyst and drying as in Procedure K yields 10.1 g of colorless (white) solid having a estimated nominal Mn content of 1.24 wt %, based on total solid weight.

Procedure O

Replicate Procedure N with changes to prepare a copper (Cu) containing catalyst. First, Substitute 582 mg (2.33 mmol) of hydrated copper sulfate $(CuSO_4.5H_2O$ (commercially available from Aldrich) for the hydrated manganese sulfate. Dissolution as in Procedure N yields a blue solution. Preparation of wetted catalyst and drying as in Procedure N yields 10.1 g of light greenish-blue solid having a estimated nominal Cu content of 1.48 wt %, based on total solid weight.

Procedures P and Q

Preparation of Barium Sulfate $(BaSO_4)$ Catalyst Support

Charge 1200 mL of deionized water, 72 g of barium chloride $(BaCl_2)$ and 86 g of sodium dodecylbenzene sulfonate into a 2 liter (L) 3-neck flask that contains a stirring bar and fitted with a reflux condenser and an equalizing addition funnel, and seated in a heating mantle. With stirring, heat contents of the flask to a set point temperature of 85° C., then charge 50.5 ml of dimethyl sulfate dropwise to the flask via the addition funnel at a rate sufficient to minimize, preferably eliminate, excess foaming and heat liberation. In the 2 L flask, addition over a period of two hours provides satisfactory results. Skilled artisans recognize that use of a larger volume container may allow one to add the dimethyl sulfate at a much faster rate.

After completing dimethyl sulfate addition, continue stirring flask contents at the set point temperature of 85° C. for 36 hours, and then allow the flask contents to cool to ambient temperature and settle over a period of 18 hours. Collect solid contents of the flask by decanting and centrifuge. Wash the solid contents twice by suspending them in a 10 ml per gram of solids, 2:1 volume/volume mixture of diethyl ether and ethanol, decanting and centrifuge. Following the second wash, decant and centrifuge procedure, dry the solid contents at a set point temperature of 70° C. until they appear dry to touch. The drying temperature is not critical, with temperatures ranging from ambient to 100° C. providing satisfactory results, adjusted for time with a longer time needed at ambient than at 70° C. or 100° C.

Dodecylbenzene Sulfonate Removal Procedure 1

Suspend a portion of the porous mesostructured $BaSO_4$ catalyst support in a 2:1 volume/volume mixture of ethanol and diethyl ether with stirring for 30 minutes. The amount of ethanol/diethyl ether mixture is not critical as long as it forms a suspension of the catalyst support. Centrifuge flask contents, then decant liquid from the flask. Repeat the foregoing procedure a second time.

Dodecylbenzene Sulfonate Removal Procedure 2

Replicate dodecylbenzene sulfonate removal procedure 1 with changes. First, substitute a 5:1 (weight/weight) mixture of ethanol and concentrated hydrochloric acid for the ethanol/diethyl ether mixture. Second, after the second centrifuge extraction, suspend solids twice in diethyl ether, then centrifuge suspended solids, decant diethyl ether from solids and air dry solids.

Dodecylbenzene Sulfonate Removal Procedure 3

Suspend an amount of the $BaSO_4$ catalyst support in reagent grade acetone and heat the suspended support/acetone mixture to reflux with stirring for 18 hours. After cooling to ambient temperature, centrifuge the mixture to collect solids from the mixture and air dry the solids.

Each of the dodecylbenzene sulfonate removal procedures provides an essentially quantitative recovery of porous mesostructured $BaSO_4$ catalyst support.

Impregnation with Pd (Procedure P)

Prepare a paste using a solution of 0.32 g of palladium acetate in 15 mL of water and 5 g of $BaSO_4$ prepared using dodecyl benzene sulfonate removal procedure 3. Dry the paste overnight at a set point temperature of 70° C. As with preparation of the support, one may readily adjust time and temperature as desired without departing from the spirit or scope of this invention as long as one attains a low enough moisture content to facilitate grinding. Grind the dried paste so ground solids pass through a #45 sieve (354 micrometer (μm sieve opening). The ground solids have a nominal Pd metal content of 3 wt %, based on total ground solids weight.

Impregnation with Pd (Procedure Q)

Replicate Procedure P with changes to substitute 0.48 g of vanadyl sulfate ($VOSO_4$) for the palladium acetate. The ground solids have a nominal V metal content of 3 wt %, based on total ground solids weight.

Ex 1

As a reaction vessel, use a 100 milliliter (mL) corrosion resistant (HASTELLOY™ C 276) Parr pressure vessel equipped with a fitting for introducing gaseous materials ($CH_4$ and nitrogen ($N_2$)) into the vessel, an internal thermocouple for measuring temperature, a transducer for measuring internal vessel pressure and a vent line for venting excess pressurized gas to a scrubber. Dry the reactor in an oven and then transfer it to a glove box having an inert gas ($N_2$) atmosphere. Charge the reactor with 0.9 grams (g) of the tan/light brown solid prepared in accord with Procedure A as catalyst then remove the reactor and its contents from the glove box. Connect the reactor to gas lines that supply the gaseous reactants, the internal thermocouple, the transducer and the vent line. Pressure test the reactor with gaseous nitrogen, then subject the reactor to a pressure/vent cycle at a temperature of 110° C. to drive out potential residual moisture that may reside in the reactor or catalyst.

Disconnect the reactor from the gas lines, thermocouple, transducer and vent line, return the reactor to the glove box, and then charge it with 5.3 g (66 millimoles (mmol)) of solid $SO_3$ (Aldrich, 227692-40G, stabilized). After sealing the reactor head to the reactor and charging the reactor with the $SO_3$, remove the reactor from the glove box, then reconnect the reactor head to the gas lines, thermocouple, transducer and vent line.

Pressurize the reactor to 508 pounds per square inch gauge (psig) (3.5 megapascals (MPa)) with $CH_4$, thereby providing a molar ratio of $CH_4:SO_3$ of 2.2/1, then heat reactor contents to a set point temperature of 150° C. and maintain the contents at that temperature for a period of 4.5 hours before allowing reactor contents to cool to ambient temperature. After cooling the reactor contents to ambient temperature, slowly vent the reactor to a 10 liter (L) TEDLAR™ bag to collect volatile components for analysis via gas chromatography (GC).

Add 15.59 g of 1N sodium hydroxide (NaOH) to the reactor contents and swirl reactor contents and NaOH to mix them together (hereinafter "Rinse 1"). Remove the Parr vessel top and pipette from the vessel a yellow-colored liquid (15.6 g) that has a pH of less than 1 and contains some solids.

Based upon analysis of two samples (1 g each) of the yellow-colored liquid via proton nuclear magnetic resonance spectroscopy ($^1H$ NMR) (200603233-15) using deuterium oxide ($D_2O$) as lock solvent and acetic acid as an internal standard, the liquid has a calculated $CH_3OX$ (where X=hydrogen (H) or a sulfonic acid ($SO_3H$) moiety) content of about 8.5 mmol. The $CH_3OX$ content equates to a yield, based upon 66 mmol of $SO_3$ as a reactant, of approximately 13 mole percent (mol %).

Replicating Ex 1, but with molecular oxygen ($O_2$) or sulfur dioxide ($SO_2$), as an oxidizing agent in place of $SO_3$, yields no detectable amounts, by $^1H$ NMR analysis, of partial oxidation products (for example methanol).

CE A

Replicate Ex 1 with changes. Replace the catalyst with 0.95 g of perfluorosulfonic acid that is used as received rather than loaded with Pd and reduce the amount of $SO_3$ to 4.45 g (56 mmol) and initial $CH_4$ pressure to 113 psig (0.8 MPa). Eliminate the pressure/vent cycle at a temperature of 110° C. to drive out potential residual moisture that may reside in the reactor or catalyst. When the reactor contents reach the set point temperature of 150° C., the pressure transducer indicates a $CH_4$ pressure of 299 psig (2.1 MPa). Add sufficient $CH_4$ to reach a $CH_4$ pressure of 595 psig (4.1 MPa), then maintain reactor contents at the set point temperature of 150° C. for 1.5 hour before heating the reactor contents to a set point temperature of 175° C. for an additional 1.5 hour. Change the amount of 1N NaOH to 15.63 g. The molar ratio of $CH_4:SO_3$ is 1:0.62.

Analysis of two 1.3 g sample aliquots of the reactor contents (16.4 g of a yellow-colored liquid that has a pH of less than one and contains some solids) as in Ex 1, results in a calculated $CH_3OX$ content of 0.39 mmol which equates to a yield, based upon 56 mmol of $SO_3$, of 0.7 mol %.

A comparison of Ex 1 yield (13 mol %) with this CE yield (0.7 mol %) demonstrates utility of including a transition metal as part of a solid, acidic catalyst material that contains an organo-sulfonic acid moiety. A yield of 0.7 mol % demonstrates that one can use a catalyst material that comprises an organo-sulfonic acid moiety, but no transition metal, to effect a limited degree of selective, partial oxidation of $CH_4$. The yield, while demonstrating that selective partial oxidation does occur to some extent, is low enough that it, and any other yield less than or equal to 1 mol %, may be regarded by many as economically unattractive. The higher 13 mol % yield, while not optimized, is far more attractive from an economic point of view.

Ex 2 through 18 and Comp Ex or CE B through M

Replicate Ex 1 with variations as shown in Table 1 below to provide CH$_3$OX yields, as shown in Table 2 below. "Rinse 2" substitutes deionized water for the 1N NaOH used in Rinse 1. Ex 10, 12, 13 and 14, CE D, CE G, and CE H use a modification wherein the catalyst is placed in a basket.

The catalyst basket (available from Wewark Wire Company) has an open top and consists of a Hastelloy™ C 200 mesh screen with a height of two centimeters (2 cm) and a width of 2.5 cm. After adding catalyst to the basket, secure the basket top tightly against the Parr vessel lid using a 10 cm length of Inconel™ wire that is wrapped around and under the basket and through a port on the vessel lid.

Ex 13, Ex 14 and CE H use a modification wherein one uses a 2.5 cm by 0.8 cm polytetrafluoroethylene (Teflon®) coated, magnetically-driven stir bar within the catalyst basket to agitate catalyst disposed therein. Effect rotation of the stir bar at a rate of approximately 850 revolutions per minute (rpm) using a Super Magnetic™ Stirrer (Cole Parmer) equipped with a digital RPM readout.

TABLE 1

| Ex/CE No | Procedure or Catalyst | Cat (g) | SO$_3$ (g) | N$_2$ P psig | CH$_4$ P psig | CH$_4$ T °C. | CH$_4$:SO$_3$ molar ratio | Rxn T °C. | Hrs at T | Rinse |
|---|---|---|---|---|---|---|---|---|---|---|
| 2 | D | 0.8 | 4.9 | 260 | 204 | 20 | 0.9 | 200 | 15 | 2 |
| 3 | A | 1.3 | 3.8 | 89 | 122 | 20 | 0.7 | 150 | 17 | 2 |
| 4 | A | 1.0 | 6.2 | 99 | 386 | 22 | 1.4 | 175 | 15 | 2 |
| B | D | 0.2 | 4.1 | 104 | 294 | 23 | 1.6 | 150 | 15 | 2 |
| 5 | A | 1.1 | 4.0 | 109 | 449 | 25 | 2.5 | 125 | 63 | 2 |
| 6 | J | 1.0 | 4.6 | 100 | 457 | 22 | 2.2 | 175 | 14 | 2 |
| 7 | G | 1.0 | 4.7 | 94 | 470 | 22 | 2.2 | 175 | 5.5 | 1 |
| C | C | 0.4 | 4.3 | 97 | 448 | 27 | 2.3 | 175 | 108 | 1 |
| D | C | 0.45 | 3.4 | 0.0 | 386 | 22 | 2.6 | 175 | 60 | 1 |
| 8 | A | 1.05 | 4.8 | 0.0 | 359 | 18 | 1.7 | 150 | 0.5 | 1 |
| E | E | 0.97 | 4.6 | 0.0 | 576 | 22 | 2.8 | 150 | 4.5 | 1 |
| F | F | 1.00 | 4.7 | 0.0 | 588 | 22 | 2.8 | 150 | 4.5 | 1 |
| 9 | C | 1.05 | 4.4 | 0.0 | 592 | 26 | 3.0 | 150 | 4.5 | 1 |
| 10 | B | 1.05 | 4.7 | 0.0 | 586 | 21 | 2.8 | 150 | 4.5 | 1 |
| G | H | 0.98 | 5.0 | 0.0 | 494 | 21 | 2.2 | 150 | 4.5 | 1 |
| 11 | B | 0.95 | 5.3 | 0.0 | 511 | 19 | 2.2 | 150 | 4.5 | 1 |
| 12 | I | 1.02 | 5.0 | 0.0 | 502 | 17 | 2.3 | 150 | 4.5 | 1 |
| 13 | B | 0.95 | 5.1 | 0.0 | 533 | 149 | 1.7 | 150 | 4.5 | 1 |
| H | K | 0.95 | 5.0 | 0.0 | 546 | 148 | 1.7 | 150 | 4.5 | 1 |
| 14 | L | 0.96 | 4.9 | 0.0 | 513 | 147 | 1.7 | 150 | 4.5 | 1 |
| 15 | B | 1.0 | 4.9 | 0.0 | 497 | 19 | 2.3 | 150 | 4.5 | 1 |
| 16 | B | 1.0 | 2.5 | 0.0 | 541 | 20 | 4.9 | 150 | 2 | 1 |
| 17 | B | 1.0 | 10.0 | 0.0 | 501 | 20 | 1.1 | 150 | 2 | 1 |
| I | B | 1.0 | 10.1 | 253 | 252 | 28 | 0.5 | 150 | 2 | 1 |
| J | M | 1.0 | 4.6 | 0.0 | 502 | 20 | 2.5 | 150 | 4.5 | 1 |
| K | N | 1.0 | 4.7 | 0.0 | 497 | 22 | 2.4 | 150 | 4.5 | 1 |
| L | O | 1.0 | 4.8 | 0.0 | 493 | 21 | 2.3 | 150 | 4.5 | 1 |
| 18 | P | 1.0 | 4.9 | 0 | 510 | 21 | 2.3 | 150 | 4.5 | 1 |
| M | Q | 1.1 | 5.7 | 0 | 495 | 23 | 1.9 | 150 | 4.5 | 1 |

TABLE 2

| Ex/CE No | CH$_3$OX mmol | Others mmol | CH$_3$OX mol % yield, vs. CH$_4$ | others mol % yield, vs. CH$_4$ | CH$_3$OX mol % yield, vs. SO$_3$ | others % yield, vs. SO$_3$ |
|---|---|---|---|---|---|---|
| 2 | 1.47 | 0.01 | 2.55 | 0.01 | 2.40 | 0.01 |
| 3 | 5.71 | 0.00 | 16.55 | 0.01 | 12.00 | 0.01 |
| 4 | 7.74 | 1.16 | 7.14 | 1.07 | 10.00 | 1.50 |
| B | 0.01 | 0.00 | 0.01 | 0.00 | 0.01 | 0.00 |
| 5 | 2.75 | 0.00 | 2.20 | 0.00 | 5.50 | 0.00 |
| 6 | 0.86 | 0.01 | 0.67 | 0.00 | 1.50 | 0.01 |
| 7 | 1.76 | 1.17 | 1.33 | 0.89 | 3.00 | 2.00 |
| C | 0.00 | 0.27 | 0.00 | 0.22 | 0.00 | 0.50 |
| D | 0.21 | 0.00 | 0.20 | 0.00 | 0.50 | 0.01 |
| 8 | 2.10 | 0.01 | 2.05 | 0.01 | 3.50 | 0.01 |
| E | 0.57 | 0.57 | 0.36 | 0.36 | 1.00 | 1.00 |
| F | 0.06 | 0.18 | 0.04 | 0.11 | 0.10 | 0.30 |
| 9 | 2.47 | 0.01 | 1.51 | 0.00 | 4.50 | 0.01 |
| 10 | 3.82 | 0.00 | 2.31 | 0.00 | 6.50 | 0.00 |
| G | 0.62 | 0.00 | 0.45 | 0.00 | 1.00 | 0.00 |
| 11 | 5.96 | 0.01 | 4.11 | 0.00 | 9.00 | 0.01 |
| 12 | 0.93 | 0.62 | 0.65 | 0.43 | 1.50 | 1.00 |
| 13 | 3.47 | 0.01 | 3.31 | 0.01 | 5.50 | 0.01 |
| H | 0.62 | 1.24 | 0.58 | 1.15 | 1.00 | 2.00 |
| 14 | 1.22 | 1.22 | 1.21 | 1.21 | 2.00 | 2.00 |
| 15 | 3.98 | 0.01 | 2.82 | 0.00 | 6.50 | 0.01 |
| 16 | 2.19 | 0.00 | 1.43 | 0.00 | 7.00 | 0.01 |

TABLE 2-continued

| Ex/CE No | CH₃OX mmol | Others mmol | CH₃OX mol % yield, vs. CH₄ | others mol % yield, vs. CH₄ | CH₃OX mol % yield, vs. SO₃ | others % yield, vs. SO₃ |
|---|---|---|---|---|---|---|
| 17 | 3.75 | 1.25 | 2.64 | 0.88 | 3.00 | 1.00 |
| I | 0.63 | 0.13 | 0.91 | 0.18 | 0.50 | 0.10 |
| J | 0.17 | 0.01 | 0.12 | 0.00 | 0.30 | 0.01 |
| K | 0.18 | 0.01 | 0.13 | 0.00 | 0.30 | 0.01 |
| L | 0.06 | 0.00 | 0.04 | 0.00 | 0.10 | 0.00 |
| 18 | 0.92 | 0.61 | 0.64 | 0.43 | 1.50 | 1.00 |
| M | 0.01 | 0.01 | 0.01 | 0.01 | 0.01 | 0.01 |

The results shown in Table 2 above support several observations, especially when such results combine with the results of Ex 1 and CE A above. First, the catalyst prepared in accord with Procedure A or Procedure B (Pd-loaded perfluorosulfonic acid catalyst) produces results that exceed results obtained from use of other metals on Nafion SAC-13 SAC catalysts. See for example Ex 1, Ex 3, Ex 4, Ex 11 and Ex 16 relative to Ex 2 (Procedure D, V-loaded catalyst). Second, a Pd supported perfluorsulfonic acid catalyst, as in Ex 1, provides superior results to an alternate catalyst support for Pd such as the sulfonated zirconium hydroxide used in Ex 7 (Procedure G). Third, small scale experiments, such as those presented herein, lead to some variability in reproducing results as evidenced by Ex 1 and Ex 11. Fourth, a low loading of Pd, as in Ex 14 (0.54 wt %) leads to a reduced CH₃OX yield relative to a higher loading as in Ex 1 (2.4 wt %) or Ex 2 (1.1 wt %). Fifth, Procedure C (catalyst doping (or treatment) with 1N H₂SO₄) appears to adversely affect CH₃OX production as shown in Ex 9 (4.5 wt % CH₃OX) versus Ex 11 (9.0 wt % CH₃OX). Sixth, selective, partial oxidation of CH₄ to CH₃OX appears to occur at a substantially slower rate at 125° C. (Ex 5) than at 150° C. (Ex 1). Seventh, selective, partial oxidation of CH₄ to CH₃OX occurs over a spread of CH₄:SO₃ molar ratios as shown in Ex 1 through Ex 18.

The invention claimed is:

1. A process for selective, partial oxidization of methane, the process being a substantially solvent-free process that comprises placing sulfur trioxide and gaseous methane in operative contact with a solid, heterogenous, acidic catalyst material, wherein the solid, heterogenous, acidic catalyst material is a superacid catalyst selected from a perfluorinated organo-sulfonic acid polymer, a composite of a perfluorinated organo-sulfonic acid polymer and a porous inorganic support, and a supported catalyst, the supported catalyst comprising at least one transition metal selected from a group consisting of palladium, vanadium and cerium on a composite of a perfluorinated organo-sulfonic acid polymer and a porous inorganic support, the contact occurring at a combination of temperature, methane pressure and for a length of time sufficient to convert at least a portion of non-gaseous forms of such sulfur trioxide to gaseous sulfur trioxide and selectively and partially oxidize at least a portion of the methane to at least one partial oxidation product selected from a group consisting of methanol and sulfate esters of methanol, the temperature being less than a temperature at which the solid, acidic catalyst material becomes unstable.

2. The process of claim 1, wherein the contact occurs at a temperature of no more than about 230 ° C.

3. The process of claim 1, wherein the length of time is less than a time sufficient to effect a substantially complete conversion of methane to its full oxidation products, carbon monoxide and carbon dioxide.

4. The process of claim 3, wherein the length of time is within a range of from greater than 0.5 minute to less than or equal to 100 hours.

5. The process of claim 1, wherein the methane pressure, measured at a temperature of 150° C., lies within a range of from 25 psig (170 kilopascals KPa to 2000 psig (13,790 KPa).

6. The process of claim 1, wherein the transition metal of the supported catalyst is palladium.

7. The process of claim 6 wherein the supported catalyst has a palladium metal loading within a range of from greater than one percent by weight to less than or equal to four percent by weight, each percent by weight being based upon total supported catalyst weight.

8. The process of claim 1, wherein the porous inorganic support comprises an oxide of a metal selected from silicon, aluminum, magnesium, titanium, zirconium and mixtures thereof.

* * * * *